United States Patent [19]

Kamishita et al.

[11] 4,316,887

[45] Feb. 23, 1982

[54] COMPOSITION FOR TOPICAL APPLICATION AND METHOD FOR PREPARING THE SAME

[75] Inventors: Takuzo Kamishita; Kazuhiko Kamishita, both of Takatsuki, Japan

[73] Assignee: Toko Yakuhin Kogyo Kabushiki Kaisha, Osaka, Japan

[21] Appl. No.: 125,894

[22] Filed: Feb. 29, 1980

Related U.S. Application Data

[63] Continuation of Ser. No. 956,620, Nov. 2, 1978, abandoned.

[30] Foreign Application Priority Data

Nov. 7, 1977 [JP] Japan .................................. 52/133217

[51] Int. Cl.$^3$ ..................... A61K 31/11; A61K 31/74; A61K 31/78; A61K 31/045
[52] U.S. Cl. ......................................... 424/81; 424/78; 424/333; 424/343
[58] Field of Search ..................... 424/78, 81, 333, 343

[56] References Cited

U.S. PATENT DOCUMENTS

| | | | |
|---|---|---|---|
| 3,485,915 | 12/1969 | Gerstein et al. | 424/81 |
| 3,592,936 | 7/1971 | Marcus et al. | 424/81 |
| 3,869,546 | 3/1975 | Lund | 424/81 |
| 3,879,317 | 4/1975 | Yuel | 424/81 |
| 3,920,811 | 11/1975 | Lund | 424/81 |
| 4,003,991 | 1/1977 | Krohn et al. | 424/78 |

FOREIGN PATENT DOCUMENTS 2345161  3/1976  France .................................. 424/81

OTHER PUBLICATIONS

Drug and Cosmetic Industry, 89(6), 718–720, 763, 804, 811, 822, (1961), "Carbopol Cosmetics", Secard.
"Carbopol 934", B. F. Goodrich Co., 1957.

*Primary Examiner*—Douglas W. Robinson
*Attorney, Agent, or Firm*—Armstrong, Nikaido, Marmelstein and Kubovcik

[57] ABSTRACT

An anti-inflammatory, analgesic and anti-pruritic compositions for topical application is made by mixing an aqueous alcoholic solution of methanol or camphor with sufficient water soluble carboxyvinyl polymer to give a viscosity of 2,000 to 20,000 centipoises at 20° C., sufficient basic agent, such as an amine, to neutralize the carboxyl groups to a pH of 6.0–7.5 and a small amount of sodium chloride.

2 Claims, No Drawings

COMPOSITION FOR TOPICAL APPLICATION AND METHOD FOR PREPARING THE SAME

This is a continuation of application Ser. No. 956,620, filed Nov. 2, 1978, now abandoned.

BACKGROUND OF THE INVENTION

1. Field of the Invention

This invention relates to a preparation for topical application containing menthol and/or camphor and to a process for producing the same.

2. Description of the Prior Art

Anti-inflammatory, analgesic and anti-pruritic preparations for topical uses containing menthol and/or camphor as active ingredient(s) have heretofore been used in the form of an ointment, liniment or tincture for percutaneous applications. However, ointments feel sticky and unpleasant when applied to the skin, possibly soiling clothes, while the active ingredient applied is not always fully absorbable through the skin. Particularly at high temperatures, ointments are liable to become unstable. With liniments and tinctures, the active ingredient can be percutaneously absorbed more effectively than in ointments, but the volatile active ingredient, i.e. menthol or camphor, is volatilized by the body temperature and thus fails to give a sustained medicinal efficacy.

Methyl cellulose, carboxymethyl cellulose, etc. are known to be polymer compounds which, when applied to the skin, form a membrane. However, for use in an aqueous alcohol solution containing menthol and/or camphor, a large quantity of such a polymer compound must be incorporated into the solution to impart the desired viscosity to the resulting preparation. Additionally, when applied to the skin, the preparation requires a long time for the formation of a membrane, feels sticky and is therefore unsuitable for use.

SUMMARY OF THE INVENTION

In an attempt to overcome the drawbacks of conventional preparations, we conducted extensive research and formulated a preparation of appropriate viscosity by use of a carboxyvinyl polymer and an amine to neutralize the polymer. We found that this preparation, when applied to the skin, rapidly forms a membrane and feels comfortably free of stickiness and that the membrane formed prevents the volatilization of menthol, camphor or like active ingredient, ensuring satisfactory percutaneous absorption. The preparation was found to be eminently useful for percutaneous applications. The colloidal form of the preparation applied to the skin is broken down by small amounts of salts such as sodium chloride in the perspiration or other cutaneous excretions, which results in rapid formation of a membrane and assures the percutaneous absorption of the active ingredient with improved effectiveness.

DETAILED DESCRIPTION

Consistent preparation obtained by neutralizing an aqueous solution of carboxyvinyl polymer with a basic substance such as water-soluble organic amine undergo marked reduction in their viscosity in the presence of small amounts of sodium chloride and other salts contained in the perspiration. This is favorable in that the preparation will rapidly form membranes on the skin. Nevertheless, the preparation loses viscosity when used in a "roll-on" container having a ball fitted in one end and rollable on the skin to apply the preparation to the skin surface because the perspiration adhering to the surface of the ball during use is introduced into the contents by the rotation of the ball. The reduction in the viscosity also occurs when the preparation contained in a metal or synthetic resin tube is extruded onto the tip of finger or the skin, owing to the contact of the preparation with the perspiration on the finger or skin.

We have further carried out intensive research to obtain preparations which are usable without entailing a reduction in its viscosity from the presence of salts in the perspiration and found that a small amount of sodium chloride, when incorporated into the preparation, prevents the reduction of the viscosity of the preparation which otherwise would be caused by the perspiration and enables the preparation to satisfactorily form membranes on the skin. Thus this invention has been accomplished.

Stated more specifically, this invention provides a preparation for topical application characterized in that the preparation comprises a mixture of an aqueous solution of an alcohol containing menthol and/or camphor, an aqueous solution of a carboxyvinyl polymer and a water-soluble basic substance, the preparation further containing 0.002 to 1% by weight of sodium chloride and having a pH of 6.0 to 7.5 and a viscosity of 2,000 to 20,000 centipoises at 20° C. The invention also provides a method for preparing such preparations for topical applications.

According to this invention, ethanol is the alcohol of choice for preparing the aqueous alcoholic solution. Also usable is ethyl alcohol denatured with methanol or geraniol. Such alcohol may also be used conjointly with propylene glycol, isopropanol or like alcohol. This imparts enhanced stability and suitable viscosity to the preparation and renders the ethyl alcohol less volatile when the preparation is applied to the skin. Isopropanol is useful in forming a stabilized colloid at low temperatures. Although not limitative, propylene glycol is used usually in an amount of about 10 to about 30% by weight of the combined amount of the alcohols used.

The alcohol concentration of the aqueous alcohol solution is usually in the range of from 20 to 60% by weights as required for dissolving menthol and/or camphor and for formulating a suitably colloidal preparation.

Carboxyvinyl polymers useful in this invention are hydrophilic polymers obtained usually from an acrylic acid. Exemplary of such polymers are those commercially available under the trademarks of Carbopol 934, 940 and 941 and manufactured by B. F. Goodrich Chemical Co., U.S.A. Carboxyvinyl polymers are used in such an amount that the resulting preparation will have a viscosity of 2,000 and 20,000 centipoises at 20° C. Preparations having the desired viscosity can be obtained usually with use of about 0.1 to about 1.5% by weight of Carbopol.

Since carboxyvinyl polymers have free carboxy groups, aqueous solution of such polymers are acidic and form consistent gels when neutralized with a base. Examples of water-soluble basic substances useful in this invention for neutralizing carboxyvinyl polymers are organic amines including alkylamines such as methylamine, ethylamine and propylamine; dialkylamines such as dimethylamine, diethylamine and dipropylamine; trialkylamines such as trimethylamine, triethylamine and tripropylamine; alkanolamines such as methanolamine, ethanolamine and propanolamine; dialkanolamines such as dimethanolamine, diethanolamine and dipropanolamine and dibutanolamine; trialkanolamines such as trimethanolamine, triethanolamine, tripropanolamine and tributanolamine; and trimethylolaminomethane. An inorganic base such as an aqueous solution of ammonia is also usable if the preparation has a low alcohol concentration. Inorganic alkalis, when used at a high alcohol concentration, may possibly convert the carboxyvinyl polymer to a resin or fail to afford the desired viscosity. Thus organic bases are preferable as water-soluble basic substances. Carboxyvinyl polymers, when neutralized with water-soluble basic substances according to this invention, give gels of substantially the same viscosity irrespective of the particular basic substance used.

The neutralization of carboxyvinyl polymers with water-soluble basic substances is generally so adjusted that the resulting preparation in the form of a gel has a pH proximate to neutrality, i.e. of 6.0 to 7.5.

According to the present invention, a small amount of sodium chloride is incorporated into the preparation by adding sodium chloride to any one of the aqueous alcohol solution of menthol and/or camphor, aqueous solution of carboxyvinyl polymer and aqueous solution of water-soluble basic substance. Alternatively sodium chloride may be added to the consistent gel resulting from the addition of the water-soluble basic substance. Sodium chloride may be used in the form of crystals or an aqueous solution. When sodium chloride crystals are added to the consistent gel preparation, the gel may possibly be converted to a resin. To produce a uniform preparation, therefore, there arises the need for excessive stirring. In this case, it is preferable to use an aqueous solution of sodium chloride which permits stirring with greater ease.

For stabilization, sodium ethylenediaminetetra-acetate (sodium EDTA) may be used conjointly with sodium chloride. This leads to a full reduction in the viscosity of the gel preparation even when a smaller amount of sodium chloride is used, presumably because sodium EDTA produces the same effect as sodium chloride.

The use of sodium chloride produces a marked reduction in the initial viscosity. For example, when 0.01 g of sodium chloride is added to 100 g of a gel preparation having a viscosity of 4,000 centipoises and the mixture is stirred, the viscosity drops to 430 centipoises. When 2.9 g of sodium chloride is added to 100 g of a gel preparation with an initial viscosity of 45,000 centipoises, the viscosity is lowered to 6,000 centipoises. A further reduction of the viscosity to 630 centipoises requires a further 4.8 g addition of sodium chloride.

Experiments were conducted as described below in which sodium chloride or an aqueous solution thereof was added to gels prepared from aqueous solutions of carboxyvinyl polymers by neutralizing the solutions with triethanolamine to a pH of 7.0, and the viscosities of the gels measured. In each experiment, sodium chloride or aqueous solution thereof was added to the gel, the gel was fully stirred and the viscosity was measured at 20° C. by a C-type viscosimeter, product of Tokyo Keiki Co., Ltd., Japan. The percentages are all by weight.

EXPERIMENT 1

Sodium chloride was added to 100 g of a gel having an initial viscosity of 4,000 centipoises and containing 0.08% of carboxyvinyl polymer, and the mixture was stirred. Viscosities varied with the amount of sodium chloride added as shown below. The sodium chloride was added in increments and the viscosity was determined after each addition.

| Incremental amounts of NaCl added (g) | Viscosity (centipoises) |
| --- | --- |
| 0 | 4,000 |
| 0.002 | 2,200 |
| 0.001 | 1,650 |
| 0.001 | 1,350 |
| 0.002 | 840 |
| 0.004 | 430 |
| (Total: 0.01 g) | |

EXPERIMENT 2

In the same manner as in Experiment 1, sodium chloride was added to 100 g of a gel having an initial viscosity of 10,000 centipoises and containing 0.11% of carboxyvinyl polymer.

| Incremental amounts of NaCl added (g) | Viscosity (centipoises) |
| --- | --- |
| 0 | 10,000 |
| 0.002 | 7,000 |
| 0.002 | 4,850 |
| 0.002 | 3,600 |
| 0.002 | 2,650 |
| 0.004 | 1,650 |
| 0.004 | 1,040 |
| 0.006 | 620 |
| 0.006 | 400 |
| (Total: 0.028 g) | |

EXPERIMENT 3

In the same manner as in Experiment 1, sodium chloride was added to 100 g of a gel having an initial viscosity of 20,000 centipoises and containing 0.17% of carboxyvinyl polymer.

| Incremental amounts of NaCl added (g) | Viscosity (centipoises) |
| --- | --- |
| 0 | 20,000 |
| 0.002 | 16,800 |
| 0.002 | 14,000 |
| 0.002 | 12,000 |
| 0.004 | 8,800 |
| 0.004 | 6,000 |
| 0.008 | 3,600 |
| 0.008 | 2,300 |
| 0.010 | 1,390 |
| 0.030 | 500 |
| (Total: 0.070 g) | |

EXPERIMENT 4

In the same manner as in Experiment 1, sodium chloride was added to 100 g of a gel having an initial viscosity of 39,000 centipoises and containing 0.88% of carboxyvinyl polymer.

| Incremental amounts of NaCl added (g) | Viscosity (centipoises) |
| --- | --- |
| 0 | 39,000 |
| 0.004 | 37,800 |
| 0.004 | 37,000 |
| 0.020 | 35,500 |
| 0.100 | 30,000 |

-continued

| Incremental amounts of NaCl added (g) | Viscosity (centipoises) |
|---|---|
| 0.100 | 24,500 |
| 0.100 | 20,500 |
| 0.100 | 18,000 |
| 0.200 | 13,000 |
| 0.200 | 9,000 |
| 0.400 | 5,600 |
| 0.800 | 2,500 |
| 1.000 | 1,000 |
| 0.600 | 700 |
| 1.000 | 380 |
| (Total: 4.628 g) | |

EXPERIMENT 5

In the same manner as in Experiment 1, sodium chloride was added to 100 g of a gel having an initial viscosity of 45,000 centipoises and containing 1.2% of carboxyvinyl polymer.

| Incremental amounts of NaCl added (g) | Viscosity (centipoises) |
|---|---|
| 0 | 45,000 |
| 0.06 | 42,800 |
| 0.20 | 37,000 |
| 0.20 | 31,800 |
| 0.20 | 28,000 |
| 0.30 | 21,300 |
| 0.24 | 19,000 |
| 0.30 | 15,800 |
| 0.60 | 10,500 |
| 0.80 | 6,000 |
| 1.40 | 3,000 |
| 2.00 | 1,200 |
| 1.40 | 630 |
| (Total: 7.70 g) | |

EXPERIMENT 6

In the same manner as in Experiment 1, sodium chloride was added to 100 g of a gel having an initial viscosity of 58,000 centipoises and containing 1.6% of carboxyvinyl polymer.

| Incremental amounts of NaCl added (g) | Viscosity (centipoises) |
|---|---|
| 0 | 58,000 |
| 0.2 | 50,000 |
| 0.5 | 38,500 |
| 0.2 | 34,100 |
| 0.4 | 29,500 |
| 0.5 | 23,800 |
| 0.5 | 20,000 |
| 1.0 | 13,500 |
| 1.0 | 8,500 |
| 2.0 | 4,100 |
| 3.0 | 1,520 |
| 3.0 | 640 |
| (Total: 12.3 g) | |

EXPERIMENT 7

Quantities of a 0.9% aqueous solution of sodium chloride were added in succession to 100 g of a gel having an initial viscosity of 5,400 centipoises and containing 0.085% of carboxyvinyl polymer.

| Incremental amounts of 0.9% aq. soln. of NaCl added (cc) | Viscosity (centipoises) |
|---|---|
| 0 | 5,400 |
| 0.025 | 5,050 |
| 0.025 | 4,700 |
| 0.025 | 4,400 |
| 0.025 | 4,050 |
| 0.050 | 3,600 |
| 0.050 | 3,200 |
| 0.100 | 2,600 |
| 0.100 | 2,100 |
| 0.100 | 1,750 |
| 0.150 | 1,350 |
| 0.250 | 950 |
| 0.250 | 650 |
| 0.250 | 500 |
| (Total: 1.400 cc) | |

EXPERIMENT 8

Sodium chloride (0.02 g) was added to 100 g of a gel having an initial viscosity of 20,000 centipoises and containing 0.17% of carboxyvinyl polymer, and the mixture was stirred to obtain a gel of 5,000 centipoises. A 0.9% aqueous solution of sodium chloride was added to the gel to check the resulting gel for variations in viscosity. The results are given below.

| Incremental amounts of 0.9% aq. soln. of NaCl added (cc) | Viscosity (centipoises) |
|---|---|
| 0 | 5,000 |
| 0.25 | 4,350 |
| 0.25 | 3,800 |
| 0.25 | 3,300 |
| 0.25 | 2,850 |
| 0.25 | 2,550 |
| 0.50 | 2,000 |
| 0.50 | 1,800 |
| 1.25 | 1,100 |
| 1.25 | 750 |
| 1.25 | 500 |
| (Total: 6.00 cc) | |

EXPERIMENT 9

Sodium chloride (1.5 g) was added to 100 g of a gel having an initial viscosity of 39,500 centipoises and containing 1.0% of carboxyvinyl polymer to obtain a gel having a viscosity of 5,400 centipoises. A 0.9% aqueous solution of sodium chloride was added to the gel to check the resulting gel for variations in viscosity. The results are given below.

| Incremental amounts of 0.9% aq. soln. of NaCl added (cc) | Viscosity (centipoises) |
|---|---|
| 0 | 5,400 |
| 2.5 | 5,000 |
| 5.0 | 4,300 |
| 5.0 | 3,700 |
| 5.0 | 3,200 |
| 10.0 | 2,400 |
| 20.0 | 1,000 |
| 10.0 | 800 |
| (Total: 57.5 cc) | |

EXPERIMENT 10

A 0.9% aqueous solution of sodium chloride was added to 100 g of a gel having an initial viscosity of 20,000 centipoises and containing 0.17% of carboxyvinyl polymer. The gel was checked for variations in viscosity with the results given below.

| Incremental amounts of 0.9% aq. soln. of NaCl added (cc) | Viscosity (centipoises) |
| --- | --- |
| 0 | 20,000 |
| 0.25 | 16,200 |
| 0.25 | 13,000 |
| 0.25 | 10,800 |
| 0.25 | 7,600 |
| 0.25 | 6,400 |
| 0.25 | 5,400 |
| 0.25 | 4,650 |
| 0.25 | 3,900 |
| 0.25 | 3,400 |
| 0.50 | 2,600 |
| 0.50 | 1,850 |
| 0.50 | 1,500 |
| 0.75 | 1,100 |
| 0.75 | 820 |
| 0.75 | 600 |
| (Total: 6.00 cc) | |

EXPERIMENT 11

Sodium chloride (0.403 g) was added to 100 g of a gel having an initial viscosity of 39,000 centipoises and containing 0.88% of carboxyvinyl polymer to obtain a gel having a viscosity of 19,500 centipoises. A 0.9% aqueous solution of sodium chloride was added to the gel, and the gel was checked for variations in viscosity. The results are given below.

| Incremental amounts of 0.9% aq. soln. of NaCl added (cc) | Viscosity (centipoises) |
| --- | --- |
| 0 | 19,500 |
| 2.5 | 18,500 |
| 5.0 | 16,000 |
| 10.0 | 11,700 |
| 10.0 | 7,650 |
| 10.0 | 5,650 |
| 10.0 | 4,000 |
| 10.0 | 2,900 |
| 10.0 | 2,200 |
| 20.0 | 1,100 |
| 20.0 | 630 |
| (Total: 107.5 cc) | |

EXPERIMENT 12

Sodium chloride (2.6 g) was added to 100 g of a gel having an initial viscosity of 58,000 centipoises and containing 1.6% of carboxyvinyl polymer to obtain a gel having a viscosity of 18,500 centipoises. A 0.9% aqueous solution of sodium chloride was added to the gel, and the gel was checked for variations in viscosity, with the results given below.

| Incremental amounts of 0.9% aq. soln. of NaCl added (cc) | Viscosity (centipoises) |
| --- | --- |
| 0 | 18,500 |
| 5.0 | 16,700 |
| 10.0 | 13,800 |
| 15.0 | 9,500 |
| 15.0 | 6,200 |
| 15.0 | 4,700 |
| 25.0 | 2,750 |
| 25.0 | 1,800 |
| 40.0 | 820 |
| 25.0 | 560 |
| (Total: 175.00 cc) | |

Variations in viscosity due to the presence of an alcohol and variations in viscosity due to the addition of sodium chloride were investigated with the following results.

EXPERIMENT 13

A 200 g quantity of ethyl alcohol denaturated with geraniol, 560 g of purified water and 80 g of 1% aqueous solution of carboxyvinyl polymer were mixed together, and 158 g of 1% aqueous solution of triethanolamine was added to the mixture with stirring. A small amount of deionized water was further added to the resulting mixture to obtain 1,000 g of a gel having a carboxyvinyl polymer concentration of 0.08%, an alcohol concentration of 20% and a viscosity of 2,000 centipoises.

Quantities of a 0.9% aqueous solution of sodium chloride were added in succession to the gel, resulting in the following variations in viscosity.

| Incremental amounts of 0.9% aq. soln. of NaCl added (cc) | Viscosity (centipoises) |
| --- | --- |
| 0 | 2,000 |
| 1.5 | 1,250 |
| 1.25 | 920 |
| 1.25 | 680 |
| 0.625 | 600 |
| (Total: 4.625 cc) | |

EXPERIMENT 14

In the same manner as in Experiment 13, 1,000 g of a gel having an alcohol concentration of 20%, a carboxyvinyl polymer concentration of 0.19% and a viscosity of 20,000 centipoises was tested.

| Incremental amounts of 0.9% aq. soln. of NaCl added (g) | Viscosity (centipoises) |
| --- | --- |
| (Initial) | 20,000 |
| 2.5 | 16,500 |
| 2.5 | 12,000 |
| 2.5 | 8,800 |
| 2.5 | 7,000 |
| 2.5 | 5,700 |
| 2.5 | 4,800 |
| 2.5 | 4,000 |
| 5.0 | 2,800 |
| 5.0 | 2,000 |
| 5.0 | 1,770 |
| 7.5 | 1,100 |
| 7.5 | 800 |
| 7.5 | 600 |
| (Total: 55.0 g) | |

EXPERIMENT 15

A 200 g quantity of ethyl alcohol denatured with geraniol, 400 g of deionized water and 240 g of 4% aqueous solution of carboxyvinyl polymer was mixed together, and 130 g of 10% aqueous solution of triethanolamine was added to the mixture to obtain a uniform gel having a viscosity of 40,000 centipoises. A 25 g quantity of 10% aqueous solution of sodium chloride was slowly added to the gel with stirring, and a small amount of deionized water was further added to the gel to obtain 1,000 g of a gel having a viscosity of 20,000 centipoises and a carboxyvinyl polymer concentration of 0.96%.

An aqueous solution of sodium chloride was added to the gel with the following results.

| Incremental amounts of 0.9% aq. soln. of NaCl added (g) | Viscosity (centipoises) |
|---|---|
| 0 | 20,000 |
| 25 | 18,000 |
| 125 | 12,000 |
| 125 | 6,800 |
| 125 | 4,700 |
| 125 | 3,100 |
| 250 | 1,300 |
| 125 | 900 |
| 125 | 600 |
| (Total: 1,025 g) | |

EXPERIMENT 16

In the same manner as in Experiment 13, 1,000 g of a gel was prepared which had an alcohol concentration of 60%, a carboxyvinyl polymer concentration of 0.125% and a viscosity of 2,000 centipoises. An aqueous solution of sodium chloride was added to the gel with the following results.

| Incremental amounts of 0.9% aq. soln. of NaCl added (g) | Viscosity (centipoises) |
|---|---|
| 0 | 2,000 |
| 1.5 | 1,100 |
| 1.25 | 600 |
| (Total: 2.75 g) | |

EXPERIMENT 17

In the same manner as in Experiment 13, 1,000 g of a gel was prepared which had an alcohol concentration of 60%, a carboxyvinyl polymer concentration of 0.38% and a viscosity of 20,000 centipoises. An aqueous solution of sodium chloride was added to the gel with the following results.

| Incremental amounts of 0.9% aq. soln. of NaCl added (g) | Viscosity (centipoises) |
|---|---|
| 0 | 20,000 |
| 2.5 | 16,000 |
| 2.5 | 14,000 |
| 2.5 | 11,000 |
| 2.5 | 8,200 |
| 2.5 | 7,100 |
| 2.5 | 6,200 |
| 5.0 | 4,600 |
| 5.0 | 3,700 |
| 5.0 | 2,600 |
| 5.0 | 1,800 |
| 5.0 | 1,400 |
| 5.0 | 1,100 |
| 5.0 | 900 |
| 5.0 | 750 |
| 5.0 | 600 |
| (Total: 60.0 g) | |

EXPERIMENT 18

A 600 g quantity of alcohol denatured with geraniol, 120 g of deionized water and 255 g of 4% aqueous solution of carboxyvinyl polymer were mixed together, and 15 g of triethanolamine was added to the mixture to obtain a uniform gel having a viscosity of 40,000 centipoises. A 5.4 g quantity of 10% aqueous solution of sodium chloride was slowly added to the gel with stirring, and a small amount of deionized water was added to the resulting mixture to prepare 1,000 g of a gel having a viscosity of 20,000 centipoises and a carboxyvinyl polymer concentration of 1.12%. An aqueous solution of sodium chloride was added to the gel with the following results.

| Incremental amounts of 0.9% aq. soln. of NaCl added (g) | Viscosity (centipoises) |
|---|---|
| (Initial) | 20,000 |
| 20 | 17,000 |
| 100 | 5,600 |
| 40 | 4,800 |
| 40 | 4,000 |
| 80 | 3,000 |
| 80 | 2,200 |
| 80 | 1,400 |
| 80 | 1,130 |
| 120 | 850 |
| 120 | 600 |
| (Total: 760 g) | |

The experiments described above reveal that the use of sodium chloride reduces the viscosity of preparations similarly irrespective of whether they contain alcohol (ethyl alcohol). When the preparation has a high alcohol content and a high initial viscosity (the viscosity of the gel free from sodium chloride) a smaller amount of sodium chloride is required for giving a reduced viscosity since the water content is low. At a higher alcohol content, there is the necessity of using a larger amount of carboxyvinyl polymer to give a preparation of specified viscosity.

Table 1 below shows amounts (in % by weight) of carboxyvinyl polymer needed for forming gel preparations having the same viscosity.

TABLE 1

| Viscosity of gel preparation (centipoises) | Alcohol concentration in preparation (% by weight) | | |
|---|---|---|---|
| | 0% | 20% | 60% |
| 4,000 | 0.08 | 0.095 | 0.187 |
| 20,000 | 0.17 | 0.19 | 0.38 |
| 40,000 | 0.88 | 0.96 | 1.12 |

Table 2 below shows quantities (in % by weight) of sodium chloride required for producing the same reduction in the viscosities of gel preparations containing varying amounts of alcohol.

TABLE 2

| Viscosity of gel preparation (centipoises) | | Alcohol concentration in preparation (wt. %) | | |
|---|---|---|---|---|
| Initial | Final | 0% | 20% | 60% |
| 4,000 | 2,000 | 0.0022 | 0.0021 | 0.0023 |
| 40,000 | 20,000 | 0.366 | 0.25 | 0.054 |

The topical preparations containing menthol and/or camphor as active ingredient(s) and contemplated by this invention may further incorporate an antiseptic or disinfectant such as thymol, local anesthetic such as ethyl aminobenzoate, rubefacient (vasodilator) such as vanillyl-n-nonylamide, antihistamine such as chlorpheniramine, etc. When so desired.

The topical preparations of this invention are produced by adding menthol and/or camphor to an aqueous solution of alcohol to prepare a uniform solution with stirring, adding an aqueous solution of carboxyvinyl polymer to the uniform solution and finally adding a water-soluble basic substance or aqueous solution thereof to the resulting mixture with full stirring. In this process sodium chloride or an aqueous solution thereof is added to any one of the aqueous alcohol solution, the aqueous carboxyvinyl polymer solution, the aqueous solution of water-soluble basic substance and the consistent gel preparation obtained.

It is desirable that the topical preparations of this invention have a viscosity of 2,000 to 20,000 centipoises, preferably 4,000 to 8,000 centipoises, so as to be applicable to the skin especially by the rotation of a ball. When having a viscosity of more than 8,000 centipoises, the preparations are suited for use as contained in jars or tubes.

As will be apparent from the foregoing experiments, use of a very small amount of sodium chloride produces a marked viscosity reduction in gel preparations having a low initial viscosity, whereas in the case of gel preparations whose viscosity has been reduced from a high level to a given level with the addition of sodium chloride, further addition of sodium chloride or an aqueous solution thereof results in only a moderate reduction in viscosity. This is also the case with gel preparations incorporating alcohol, or menthol- and/or camphor-containing alcohol although the viscosity reduction achieved is greater.

When the preparation is applied to the skin by a ball by virtue of its rotation, the perspiration will be transferred onto the ball surface, but the perspiration will not seriously reduce the viscosity of the preparation if the preparation contains an increased amount of sodium chloride. However, it is desired that the preparations of this invention, when applied to the skin, form a membrane without giving a feel of stickiness as do ointments. Further when the preparation is used as contained in a jar or tube, the perspiration or the like adhering to the tip of a finger would degrade the preparation due to the resulting reduction in the viscosity of the remaining preparation, but the use of sodium chloride prevents such degradation.

In order to fulfill these two requirements, namely the prevention of the reduction in the viscosity of the preparation and the breakdown of the gel form on the skin or formation of a membrane, it is preferable to incorporate up to 1% by weight of sodium chloride in the preparation, whereas if used in a very small amount, sodium chloride will not fully produce the desired effect (prevention of viscosity reduction in the preparation remaining in the container). Thus sodium chloride must be used in an amount of at least 0.002% by weight. To obtain gel preparations containing 0.002 to 1% by weight of sodium chloride and having a viscosity of 2,000 to 20,000 centipoises, the carboxyvinyl polymer is used in an amount of 0.1 to 1.5% by weight.

The gel preparations prepared by the method of this invention have viscosities of 2,000 to 20,000 centipoises at 20° C. and are in the form of an approximately neutral, transparent and semi-fluid colloid. The preparations are stable at a relatively high temperature (40° C.) or at a low temperature (10° C.) and undergo little or no variations in viscosity. In fact, they remain very stable and free of viscosity variations even when allowed to stand at 40° C. for 6 months.

When the present preparations are applied to the skin, a membrane of carboxyvinyl polymer is rapidly formed on the skin on evaporation of alcohol, which prevents the volatilization of menthol and/or camphor. The colloidal preparation present at the interface between the carboxyvinyl polymer and the skin surface is broken down to a liquid. This assures effective percutaneous absorption of the active ingredient(s), i.e. menthol and/or camphor. The membrane of carboxyvinyl polymer subsequently formed, although very thin, is durable and covers the skin without adhering to clothes. Accordingly the present preparations have a sustained medicinal efficacy unlike conventional liniments and tinctures.

Further since the gel preparations of this invention contain sodium chloride which prevents the reduction of viscosity that would otherwise be caused by the perspiration or the like introduced into the preparation, the preparation placed in a container is fully usable until the container is completely emptied. Thus the preparations of this invention are well suited for application with a ball which, when rolled, transfers the preparation from the ball surface onto the skin. The carboxyvinyl polymer membrane is soluble in water and is therefore readily removable from the skin when washed with water.

Given below are Examples of this invention, in which water purified by use of an ion exchange resin was used as purified water or the water for aqueous solutions. The viscosities were determined at 20° C. with use of a C-type viscosimeter produced by Tokyo Keiki Co., Ltd., Japan. The percentages are all by weight.

EXAMPLE 1

A 60 g quantity of l-menthol, 40 g of dl-camphor, 5 g of thymol and 0.2 g of vanillyl-n-nonylamide were dissolved in 350 g of 95% alcohol denaturated with geraniol to prepare a uniform solution with stirring. Propylene glycol (100 g) and 80 g of isopropyl alcohol were added to the solution, the mixture was stirred and 280 g of 5% aqueous solution of carboxyvinyl polymer was added to the mixture. The resulting mixture was stirred. With addition of 18.9 g of triethanolamine, the mixture was fully stirred, giving a consistent gel having a viscosity of 40,000 centipoises and a pH of 7.20.

A 5.6 g quantity of 10% aqueous solution of sodium chloride and 60 g of purified water were added to the gel, and the mixture was stirred. With addition of a small amount of purified water, the mixture was further thoroughly stirred to obtain 1,000 g of a uniform gel preparation having a viscosity of 10,000 centipoises, a pH of 7.20 and a carboxyvinyl polymer concentration of 1.4% and containing 0.056% of sodium chloride.

EXAMPLE 2

A 60 g quantity of l-menthol, 40 g of dl-camphor, 5 g of thymol and 0.2 of vanillyl-n-nonylamide were dissolved in 350 g of 95% alcohol denaturated with geraniol, 100 g of propylene glycol and 80 g isopropyl alcohol were added to the solution, and the mixture was thoroughly stirred. With addition of 200 g of 5% aqueous solution of carboxyvinyl polymer, the resulting solution was stirred. Subsequently 13.5 g of triethanolamine and 150 g of purified water were added to the mixture. The mixture was stirred, affording a consistent gel having a viscosity of 30,000 centipoises and a pH of 6.95. A 4 g quantity of 10% aqueous solution of sodium chloride and a small amount of purified water were added to the gel, and the mixture was thoroughly stirred to obtain 1,000 g of a uniform gel preparation having a viscosity of 10,000 centipoises, a pH of 6.91 and a carboxyvinyl polymer concentration of 1% and containing 0.04% of sodium chloride.

EXAMPLE 3

A 60 g quantity of l-menthol, 40 g of dl-camphor, 5 g of thymol and 0.2 g of vanillyl-n-nonylamide were dissolved in 350 g of 95% alcohol denaturated with geraniol, 100 g of propylene glycol and 80 g of isopropyl alcohol were added to the solution, and 350 g of 1% aqueous solution of carboxyvinyl polymer was further added to the solution. The mixture was stirred. Addition of 4.7 g of triethanolamine thereto with stirring gave a consistent gel having a viscosity of 15,000 centipoises and a pH of 7.10. With further stirring, 1.03 g of 10% aqueous solution of sodium chloride was added to the gel. Subsequently a small amount of purified water was added to the gel, and the mixture was thoroughly stirred to obtain 1,000 g of a uniform gel having a viscosity of 5,600 centipoises, a pH of 7.10 and a carboxyvinyl polymer concentration of 0.35% and containing 0.0103% of sodium chloride. To the gel was added 0.9% aqueous solution of sodium chloride in small portions with stirring. The resulting variations in viscosity are listed below.

| Incremental amounts of 0.9% aq. soln. of NaCl added (g) | Viscosity (centipoises) |
| --- | --- |
| 0 | 5,600 |
| 1 | 5,450 |
| 2 | 5,200 |
| 2 | 5,000 |
| 4 | 4,600 |
| 4 | 4,200 |
| 8 | 3,600 |
| 10 | 2,900 |
| 10 | 2,450 |
| 10 | 2,000 |
| 10 | 1,800 |
| (Total: 61 g) | |

EXAMPLE 4

A 60 g quantity of l-menthol, 40 g of dl-camphor, 5 g of thymol and 0.2 g of vanillyl-n-nonylamide were dissolved in 350 g of 95% alcohol denaturated with geraniol, 80 g of isopropyl alcohol and 100 g of propylene glycol were added to the solution. With addition of 180 g of 1% aqueous solution of carboxyvinyl polymer and 182 g of purified water to the solution, the resulting solution was stirred. Subsequently 2.4 g of triethanolamine and a small amount of purified water were added to the mixture. The mixture was stirred to obtain 1,000 g of consistent gel having a viscosity of 5,600 centipoises and a pH of 7.01.

To the gel was added 0.9% aqueous solution of sodium chloride in small portions with stirring. The resulting variations in viscosity are listed below.

| Incremental amounts of 0.9% aq. soln. of NaCl added (g) | Viscosity (centipoises) |
| --- | --- |
| 0 | 5,600 |
| 1.0 | 5,400 |
| 1.0 | 5,000 |
| 1.0 | 4,600 |
| 2.0 | 4,000 |
| 2.0 | 3,500 |
| 2.0 | 3,100 |
| 4.0 | 2,450 |
| 4.0 | 2,000 |
| 4.0 | 1,300 |
| 4.0 | 1,100 |
| 8.0 | 800 |
| 8.0 | 600 |
| (Total: 41.0 g) | |

EXAMPLE 5

A 60 g quantity of l-menthol, 40 g of dl-camphor, 5 g of thymol and 0.2 g of vanillyl-n-nonylamide were dissolved in 350 g of 95% alcohol denaturated with geraniol to obtain a uniform solution with stirring. To this solution, 100 g of propylene glycol and 80 g of isopropyl alcohol were added with stirring. To this mixture, 280 g of 5% aqueous solution of carboxyvinyl polymer was added and 7.74 g of monoethanolamine was further added thereto with stirring. A consistent gel having a viscosity of 40,000 centipoises and a pH of 7.15 was obtained.

To the above gel, 5.6 g of 10% aqueous solution of sodium chloride and a small amount of purified water were added with stirring to obtain 1,000 g of a uniform gel having viscosity of 10,000 centipoises and a pH of 7.13, and carboxyvinyl polymer concentration of 1.4% and containing 0.056% of sodium chloride.

EXAMPLE 6

A 60 g quantity of l-menthol, 40 g of dl-camphor, 5 g of thymol and 0.2 g of vanillyl-n-nonylamide were dissolved in 350 g of 95% alcohol denaturated with geraniol to obtain a uniform solution. To the solution, 100 g of propylene glycol and 80 g of isopropyl alcohol were added, and 350 g of 1% aqueous solution of carboxyvinyl polymer was added to the mixture with stirring. With addition of 3.5 g of triethylamine, the mixture was fully stirred, giving a consistent gel having a viscosity of 15,000 centipoises and a pH of 7.03. To this gel, 1.03 g of 10% aqueous solution of sodium chloride and a small amount of purified water were added with stirring to obtain 1,000 g of uniform gel preparation having a viscosity of 5,600 centipoises, a pH of 7.05, and a carboxyvinyl polymer concentration of 0.35% and containing 0.0103% of sodium chloride.

The resulting variations in viscosity by adding 0.9% aqueous solution of sodium chloride in small portion with stirring were almost same as the case of the Example 3.

EXAMPLE 7

A 60 g quantity of l-menthol, 40 g of dl-camphor, 5 g of thymol and 0.2 g of vanillyl-n-nonylamide were dissolved in 350 g of 95% alcohol denaturated with geraniol, 80 g of isopropyl alcohol and 100 g of propylene glycol were added to the solution. With addition of 180 g of 1% aqueous solution of carboxyvinyl polymer and 181 g of purified water to the solution, the resulting solution was stirred. Subsequently 3.06 g of diisopropanolamine and a small amount of purified water were added to the mixture. The mixture was stirred to obtain 1,000 g of consistent gel having a viscosity of 5,600 centipoises and a pH of 7.07.

To the gel was added 0.9% aqueous solution of sodium chloride in small portions with stirring. The resulting variations in viscosity were almost same as the case of the Example 4.

EXAMPLE 8

A 60 g quantity of l-menthol, 40 g of dl-camphor, 5 g of thymol and 0.2 g of vanillyl-n-nonylamide were dissolved in 350 g of 95% alcohol denaturated with geraniol, 100 g of propylene glycol and 80 g of isopropyl alcohol were added to the solution, and then 350 g of 1% aqueous solution of carboxyvinyl polymer were added with stirring. To this mixture, triethanolamine was added to obtain consistent gel having a viscosity of 15,000 centipoises and a pH of 7.20. To the gel, 1.58 g of 10% aqueous solution of EDTA.2Na, 0.53 g of 10% aqueous solution of sodium chloride and a small amount of purified water to obtain 1,000 g of uniform gel preparation having a viscosity of 5,600 centipoises, a pH of 7.20 containing 0.35% of carboxyvinyl polymer, 0.0158% of EDTA.2Na and 0.0053% of sodium chloride.

To the gel was added 0.9% aqueous solution of sodium chloride in small portions with stirring. The resulting variations in viscosity are listed below.

| Incremental amounts of 0.9% aq. soln. of NaCl added (g) | Viscosity (centipoises) |
| --- | --- |
| 0 | 5,600 |
| 1 | 5,450 |
| 2 | 5,200 |
| 2 | 5,000 |
| 4 | 4,650 |
| 4 | 4,200 |
| 8 | 3,600 |
| 10 | 2,850 |
| 10 | 2,400 |
| 10 | 2,000 |
| 10 | 1,800 |
| (Total: 61 g) | |

What we claim is:

1. A composition for topical application comprising a mixture of: (a) an aqueous solution of 20 to 60% by weight of an alcohol selected from the group consisting of ethanol, ethanol denatured with methanol, ethanol denatured with geraniol, said aqueous solution containing a therapeutically effective amount of an ingredient selected from menthol, camphor and a mixture of menthol and camphor; (b) a carboxyvinyl polymer in an amount of 0.1 to 1.5% by weight based on the weight of said composition; (c) a water-soluble basic substance selected from the group consisting of an alkylamine, a dialkylamine, a trialkylamine, an alkanolamine, a dialkanolamine, a trialkanolamine, trimethylolaminomethane, and ammonia in an amount effective for neutralizing the carboxyvinyl polymer; and (d) 0.002 to 1% by weight of sodium chloride based on the weight of said composition, said composition having a pH of 6.0 to 7.5 and a viscosity of 2,000 to 20,000 centipoises at 20° C.

2. A method for preparing a composition for topical application having a pH 6.0 to 7.5 and a viscosity of 2,000 to 20,000 centipoises at 20° C., which comprises admixing an aqueous carboxyvinyl polymer solution containing said carboxyvinyl polymer in an amount to provide 0.1 to 1.5% by weight of said carboxyvinyl polymer based on the weight of said composition with an aqueous alcoholic solution containing 20 to 60% by weight of an alcohol selected from the group consisting of ethanol, ethanol denatured with methanol, ethanol denatured with geraniol, said aqueous alcoholic solution containing a therapeutically effective amount of an ingredient selected from menthol, camphor and a mixture of menthol and camphor and adding to the resulting admixture, with stirring, a water-soluble basic substance selected from the group consisting of an alkylamine, a dialkylamine, a trialkylamine, an alkanolamine, a dialkanolamine, a trialkanolamine, trimethylolaminomethane and ammonia in an amount effective for neutralizing said carboxyvinyl polymer and adjusting the pH of the resulting system to 6.0 to 7.5, and adding sodium chloride to said resulting system in an amount to bring the sodium chloride content of said composition to 0.002 to 1% by weight.

* * * * *